United States Patent [19]
Brown et al.

[11] Patent Number: 5,683,365
[45] Date of Patent: Nov. 4, 1997

[54] TIP PROTECTION DEVICE

[75] Inventors: Herbert Brown, Colleyville, Tex.; Joseph J. Chang, Avon, Conn.; Mark Panzera, Bristol, Conn.; Thomas Sloane, West Redding, Conn.; David L. Bogert, Plainville, Conn.; Gerald J. Kovalic, Southlake, Tex.

[73] Assignee: Johnson & Johnson Medical, Inc., Arlington, Tex.

[21] Appl. No.: 482,595

[22] Filed: Jun. 7, 1995

[51] Int. Cl.⁶ .................................................. A61M 5/00
[52] U.S. Cl. ........................................ 604/110; 604/192
[58] Field of Search ................................ 604/110, 192, 604/198, 263, 187

[56] References Cited

U.S. PATENT DOCUMENTS

| | | |
|---|---|---|
| 4,117,809 | 10/1978 | Moorehead . |
| 4,762,516 | 8/1988 | Luther et al. . |
| 4,790,828 | 12/1988 | Dombrowski et al. . |
| 4,804,371 | 2/1989 | Vaillancourt . |
| 4,826,490 | 5/1989 | Byrne et al. . |
| 4,832,696 | 5/1989 | Luther et al. . |
| 4,834,718 | 5/1989 | McDonald . |
| 4,917,669 | 4/1990 | Bonaldo . |
| 4,917,672 | 4/1990 | Terndrup et al. ............... 604/192 |
| 4,931,048 | 6/1990 | Lopez . |
| 4,944,725 | 7/1990 | McDonald . |
| 4,950,252 | 8/1990 | Luther et al. . |
| 4,952,207 | 8/1990 | Lemieux . |
| 4,964,854 | 10/1990 | Luther . |
| 4,978,344 | 12/1990 | Dombrowski et al. . |
| 4,994,041 | 2/1991 | Dombrowski et al. . |
| 5,007,901 | 4/1991 | Shields . |
| 5,084,023 | 1/1992 | Lemieux . |
| 5,084,030 | 1/1992 | Byrne et al. . |
| 5,127,905 | 7/1992 | Lemieux . |
| 5,205,829 | 4/1993 | Lituchy . |
| 5,215,528 | 6/1993 | Purdy et al. . |
| 5,300,045 | 4/1994 | Plasche, Jr. .................. 604/263 |
| 5,312,371 | 5/1994 | Dombrowski et al. . |
| 5,328,482 | 7/1994 | Sircom et al. ............... 604/110 X |
| 5,334,158 | 8/1994 | McLees ........................ 604/110 |

*Primary Examiner*—John D. Yasko
*Attorney, Agent, or Firm*—Joseph F. Shirtz

[57] ABSTRACT

A safety cover which securably and reliably locks the tip of a cannula in an interior chamber within the safety cover. The cover comprises an elongate body having the interior chamber and an axial through hole which extends along the entire length of the body, through the interior chamber and through which the cannula is slidably received. Displacing elements are positioned within the interior chamber, each of which includes a hole for receiving said cannula therethrough, and which displaces upon retraction of the tip of said cannula, thereby preventing subsequent advancement of said cannula tip. In a first embodiment the displacing elements are annular rings. In a second embodiment, the elements are rigid balls having through holes. In a third embodiment, the displacing elements are a pair of conical elements, one of which is spring biased, each of which includes an offset hole. In each embodiment, it is preferable that the cannula should include a thickened rib adjacent to said tip, and the safety cover should correspondingly include an annular section in the rear portion thereof. The through hole extending through the rear portion has a diameter which is smaller than said thickened rib of said cannula whereby the cannula tip may not be retracted from the safety cover.

15 Claims, 7 Drawing Sheets

TIP PROTECTION DEVICE

BACKGROUND OF THE INVENTION

1. Field of the Invention

The present invention relates generally to stick prevention apparatus for protecting medical personnel from injury. More particularly, the present invention relates to tip covering elements having internal elements which prevent a retracted needle from reinserting therethrough.

2. Description of Prior Art

Medical care of individuals in hospitals, clinics, and other health care facilities often includes the taking of blood samples, intravenous supplying of medication, and the introduction or removal of other fluids via cannulae, needles, or syringes. The present medical environment, in which there exist diseases, for example Acquired Immune Deficiency Syndrome, AIDS, for which there are no cures, and which are transmitted via blood to blood contact, has raised concerns relating to the potential for contaminated "needle sticks".

A wide variety of devices have been provided in the prior art for prevention against accidental contaminated "needle sticks". For example, U.S. Pat. No. 5,215,528 to Purdy et al. (hereinafter Purdy) teaches an assembly for introducing a catheter into a blood vessel, wherein there is provided a tip cover. The tip cover of the Purdy device is provided with an elastically deforming L-shaped member which remains in a deformed state until the cannula is drawn back into the cover. Once retracted, the L-shaped member springs into a position to prevent reemergence of the needle. Manual repositioning of the L-shaped member is necessary to permit the cannula to reemerge from the cover U.S. Pat. No. 4,826,490 to Byrne et al. (hereinafter Byrne) teaches a safety cover and syringe assembly wherein an external cylindrical sleeve, through which the cannula extends, is slidably mounted to a track on the external surface of the syringe. Sliding the external cylindrical sleeve relative to the cannula and the syringe, such that the cannula is fully retracted into the sleeve, causes a locking mechanism to engage between the syringe and the sleeve so that the cannula may not be advanced out of the sleeve without disengagement of the locking elements by a user.

U.S. Pat. No. 5,127,905 to Lemieux teaches a protection cap, which is similar to the device disclosed by Purdy, as described above. In the Lemieux device an externally mounted rotating L-shaped lever is disposed along the axis of the cover, manual actuation of which by a user once the cannula is retracted prevents the cannula from reemerging from the cover. Manual retraction of the external L-shaped lever from the path of the cannula permits the cannula to reemerge.

The above described devices each include means for preventing "needle sticks" by interfering with the exposure of a cannula once it is retracted into a cover. In each case, however, the cannula may reemerge by removal or disengagement of the preventing means. In the devices disclosed by Purdy and Lemieux a user may retract the L-shaped element; in Byrne, the device includes a simple means for disengaging the locking elements. It is of considerable concern for users of such devices that, if a means for disengaging the retaining element is provided, random forces may expose the contaminated cannula, thus presenting a danger to medical personnel. This concern is applicable to the variety of "needle stick" prevention devices which include externally mounted prevention means.

It is, therefore, a principal object of the present invention to provide a needle cover which includes an element or elements which prevent exposure of a contaminated cannula.

It is further an object of the present invention to provide a needle cover which cannot be compromised, whereby the cannula may not reemerge therethrough, by application of random environmental forces.

It is further an object of the present invention to provide a needle cover which is more reliable in its safety aspects.

Other objects and advantages of the invention will be more fully apparent from the ensuing disclosure and appended claims.

SUMMARY OF THE INVENTION

The present invention is directed to a needle cover which includes an interior chamber and an axial path along which a cannula may extend therethrough. Within this interior chamber is a set of moveable elements which contain through holes. The elements are initially oriented so that the through holes are coaxial, and aligned with the axial path such that the cannula may extend through the cover. After use, once the cannula has become contaminated, the cannula is retracted (or the cover is advanced along the shaft of the cannula) such that the needle is removed from the through holes of the moveable elements. Once freed from the aligning influence of the cannula, the moveable elements are quickly randomized. Advance of the cannula back along the axial path is prevented by the misalignment of the elements.

A variety of embodiments of the present invention are contemplated in which the set of elements comprises, for example rings, spheres, and spring mounted interlocking conical elements. More specifically, in a first embodiment a cylindrical safety cover comprises an axial through hole which extends along the elongate axis thereof. The cover includes an inner chamber, wherein a pair of metal rings are positioned. The pair of rings have an inner diameter which is equal to or greater than the outer diameter of the cannula. In a preferred variation of this embodiment the outer diameters of each one of the pair of rings is different.

Prior to its use, a cannula is positioned through the cover, wherein the rings are disposed about the shaft of the cannula. The cannula causes the inner holes of the rings to remain coaxial. Once the cannula has been inserted into a patient and removed, the cover and cannula are moved relative to one another. Retraction of the cannula along the axial path of the cover, to a point wherein the cannula shaft is removed from the rings, causes the rings to randomize. Once randomized the rings prevent the re-emergence of the cannula.

In the preferred variations of the first embodiment, in which the corresponding outer diameters of the rings are different, randomization of the rings is enhanced by the difference in relative size.

In a second embodiment, an elongate cover, having an axial through hole and an inner chamber, similar to the one described above with respect to the first embodiment, is provided. Within the inner chamber is disposed at least one rigid ball element having a through hole. Prior to its use, the cannula is initially positioned extending through the axial through hole of the cover and the through hole of the at least one rigid ball. In this orientation the respective through holes are aligned coaxially. The cannula provides the aligning means whereby the through hole of the at least one rigid ball remain substantially coaxial with the through hole of the cover.

Once it is used, and thereby contaminated, the cannula is retracted along the through hole of the cover, and backed out of the through hole of the at least one rigid ball. Once the respective through holes of the rigid ball and the cover are no longer held coaxially aligned, the at least one rigid ball prevents the reemergence of the cannula through the cover. It is understood that a plurality of rigid balls would be preferable so that the randomization of the orientation of the plurality of balls would be significantly more difficult to overcome.

In a third embodiment, a similar cover element is provided, having a through hole and an internal chamber. A pair of nesting conical elements are provided, each comprising an offset through hole. One of the conical elements is spring mounted so that it is biased into a nesting arrangement with the other element, therein keeping the offset through holes from being coaxial. In their initial orientation, however, the conical elements are held apart, so that the offset holes may be coaxially positioned. The cannula, which is disposed through the through holes of both elements and the cover holds the conical elements in the coaxial position, against the biasing force of the spring.

Once the cannula has been used, it is retracted into the cover, and withdrawn from the through holes of the conical elements. The springs then move the conical sections into a fully nesting arrangement so that the through holes are not coaxial with one another. In a highly preferred variation of this embodiment, the spring further causes the other conical element to move so that its offset hole is also no longer coaxial with the through hole of the cover.

In each embodiment, it is also preferred that the cannula include a radially thickened rib adjacent to the tip. The forward portion of the through hole in the cover, and the through holes of the elements in the internal chamber, i.e. the rings, balls, and conical elements, are large enough for the thickened rib to be retracted therethrough. In the preferred variations, however, the rear portion of the through hole of the cover is narrow enough that only the unthickened shaft may be retracted, and the enlarged rib is prevented from being withdrawn all the way through the cover. In these variations, once the tip of the cannula has been retracted through the chamber, and is withdrawn from the through holes of the elements disposed therein, the cannula may not be advanced or further retracted, therein preventing the potential for injury and/or infection due to accidental "needle sticks".

DETAILED DESCRIPTION OF PREFERRED EMBODIMENT

Figure 1:
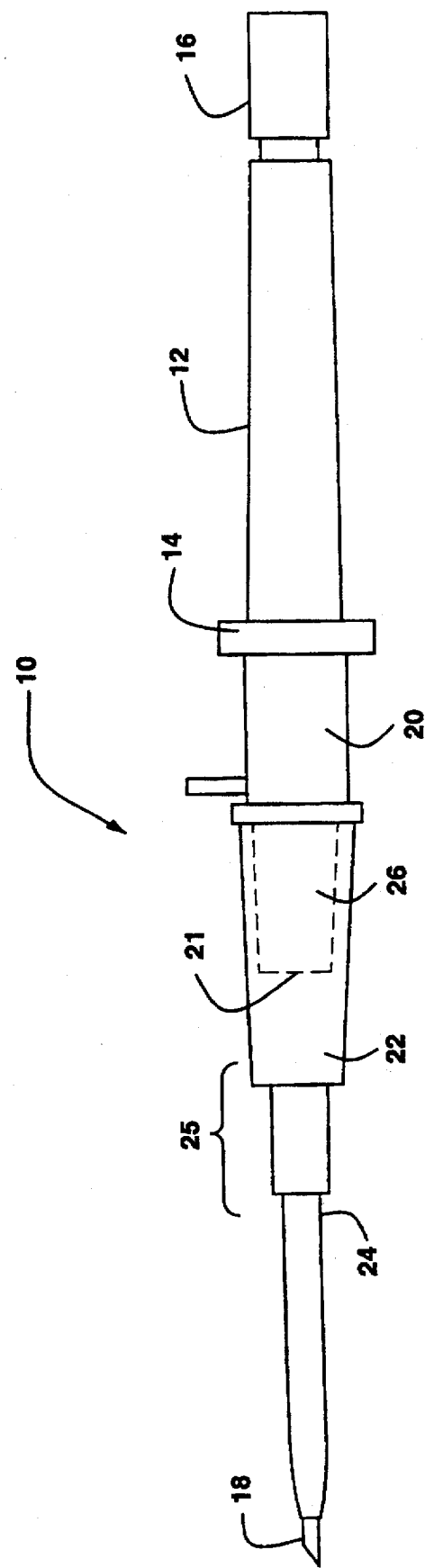
FIG. 1 is a side view of a medical assembly including a catheter, a cannula, a syringe, and the safety cover of the present invention.

This invention relates to the field of hypodermic needles and most particularly to devices for inserting catheters into blood vessels. Referring now to the drawings, FIG. 1 shows a catheter insertion apparatus 10, having a safety cover 20. The apparatus 10, which is shown in a side view, includes a syringe body 12, with an annular ring 14 at the base thereof, and a standard slidable plunger element 16 which translates within the syringe body 12. A cannula 18 extends axially outward from the annular ring 14; the narrow hollow internal passage within the cannula 18 providing a connection from the internal volume of the syringe body 12 to the exterior through which fluids may flow.

The cannula 18 extends outward from the annular ring 14 through a safety cover 20 which is constructed so that the cannula 18 may be inserted axially therethrough and so that the cannula 18 and safety cover 20 may be translated relative to each other. In the embodiment shown in FIG. 1, which is designed to insert a catheter into a blood vessel, the apparatus 10 further includes a catheter 25. The catheter 25 includes an elongate narrow, flexible, tube section 24, through which the cannula 18 is disposed prior to the catheter being inserted into the patient. The catheter 25 further includes a hub 22 having a widened receiving port 26, in which a portion of the safety cover 20 is initially nested. The nested portion 21 of the safety cover 20 is shown in phantom. The cannula 18 therefore extends outward from the annular ring 14 of the syringe body 12, sequentially through the safety cover 20, the widened receiving port 26 of the catheter hub 22, and ultimately through the elongate narrow flexible tube section 24.

In use, the cannula 18 is disposed through the narrow flexible tube section 24, to enable puncturing and insertion of the flexible tube 24 through the skin of a patient, and positioning of the tube 24 into the desired blood vessel. If properly positioned in the blood vessel, the user withdraws the cannula 18 from the patient without removing the catheter 25, therein providing an open conduit through which the medical care provider may draw blood, or input appropriate medication directly to the vasculature.

The process of removing cannulae from patients and decoupling syringes and cannulae from their corresponding catheters, in apparatus of the prior art, exposed the medical care providers to the sharp tip of the cannula 18 which had been contaminated by the patient's blood. In the present invention, the receiving port 26 of the catheter hub 22 and the external surface of the safety cover 20 are releasably mated in the initial disposition of the apparatus 10. During extraction of the syringe 10 and cannula 18, the safety cover 20 and the receiving port 26 remain coupled until the tip of the cannula 18 is fully retracted into the safety cover 20. Once the tip of the cannula 18 is fully retracted, the safety cover 20 is released from the catheter hub 22. A variety of mechanisms for releasably holding the safety cover 20 to the receiving port 26 of the catheter hub 22 are shown in the art, any one of which may be employed in the present assembly. Such releasable couplings may be manually actuatable or automatically actuated by the retraction of the tip of the cannula 18.

Figure 2:
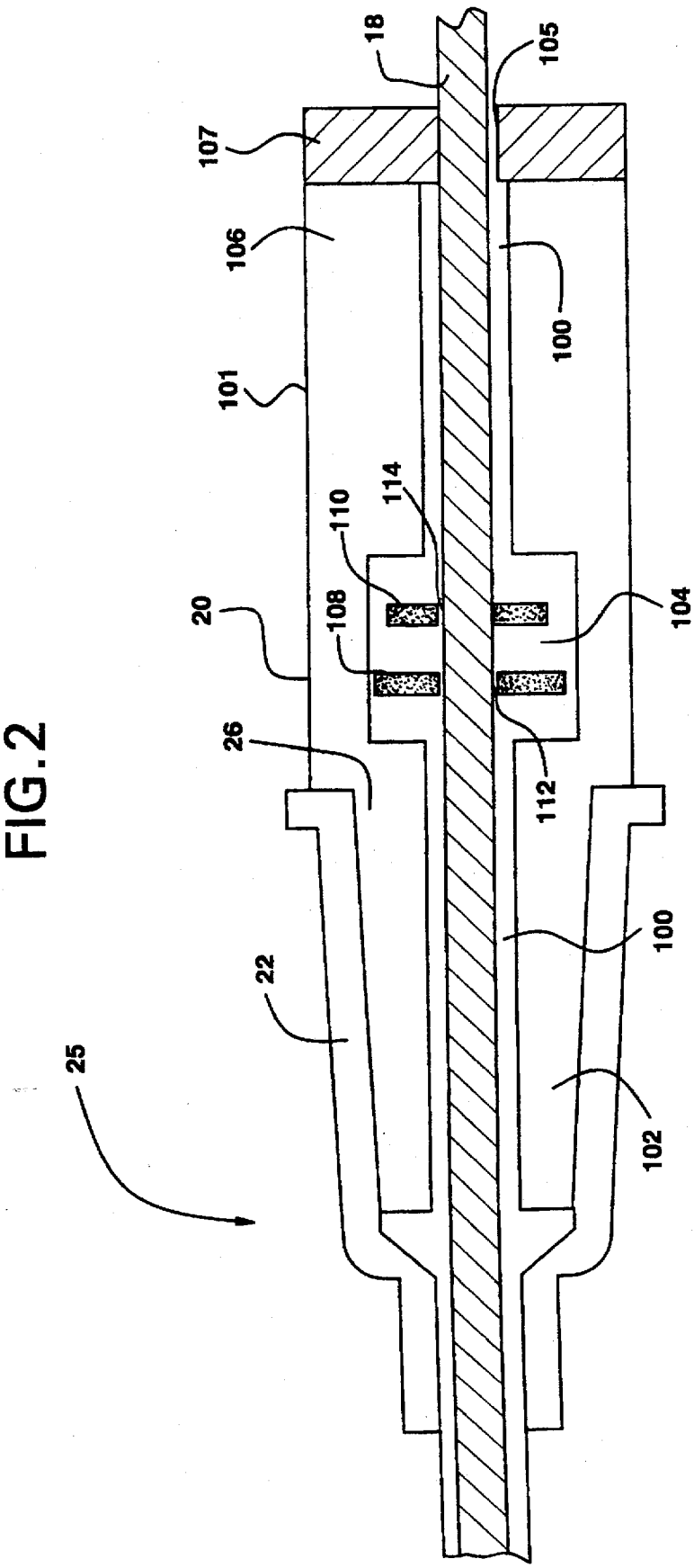
FIG. 2 is a side cross-section view of one aspect of the present invention including a pair of metal ring elements with the cannula in its initial position.

Referring now to FIG. 2, a side cross-section view of a first embodiment of the safety cover 20 of the present invention is provided wherein the cannula 18, catheter 25, and safety cover 20 are illustrated in their initial, pre-insertion, disposition. The cannula 18 extends axially through the safety cover 20 and the catheter 25, and the safety cover 20 which is nested within the receiving port 26 of the catheter hub 22.

More specifically with respect to the safety cover 20, the cover comprises an elongate and generally cylindrical body 101 having an axial through hole 100, which extends from a conical forward portion 102, through a rearward portion 106 having an interior chamber 104. The rearward portion 106 comprises a thin annular section 107 which includes a center hole 105 having a diameter which is precisely equivalent to the diameter of the cannula 18. Disposed in the interior chamber 104 is a pair of annular rings 108,110 through which the cannula 18 is initially positioned. The rings 108,110 are otherwise free to move relative to one another and within the internal chamber 104. The rings 108,110, further, preferably have different diameters.

Figure 3:
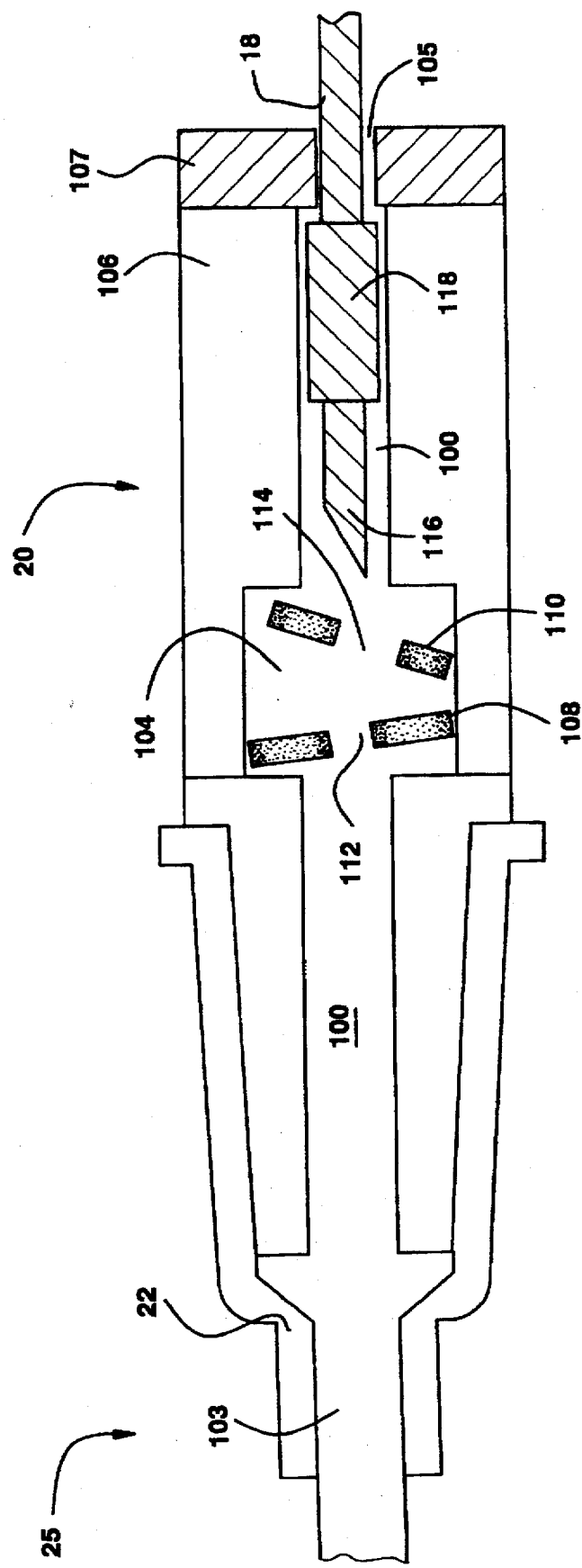
FIG. 3 is a side cross-section view of the aspect of the present invention shown in FIG. 2, wherein the cannula has been retracted and the pair of rings have randomized.

Referring now to FIG. 3, a side cross-section view of the apparatus shown in FIG. 2 is provided, wherein the cannula 18 has been retracted from the catheter hub 22. It is understood that the catheter hub 22 which is shown in FIG. 3 as remaining nested with the safety cover 20 may-have been released prior to the retraction of the cannula 18 to the position shown herein. As is shown, the retraction of the tip 116 of the cannula 18 beyond the interior chamber 104 frees the rings 108,110 from coaxial alignment with each other and the axial through hole 100 of the safety cover 20. Once freed from the axial alignment provided by the shaft of the cannula 18, the rings become randomized. The differences in ring diameters provides for enhanced randomization of the relative alignment of the passages through which the linear cannula 18 would have to be disposed.

Once the rings have randomized, the cannula 18 is prevented from advancing forwardly through the safety cover 20. In order to prevent complete back out of the cannula 18, from the safety cover 20, the tip 116 of the cannula 18 is provided with a thickened rib 118 which is spaced from the tip 116, at a distance therefrom which is less than the length from the interior chamber to a rearwardly disposed annular section 107. The axial through hole 100 (as well as the internal passage 103 of the catheter 25) has a diameter which is large enough for the thickened rib 118 to be retracted through, however, the diameter of the center hole 105 of the rearwardly disposed annular section 107 is too narrow for the thickened rib 118 to pass through. As a result, the tip 116 is prevented from fully retracting out of the safety cover 20, but can be retracted far enough that the rings may be freed to randomize.

Figure 4:
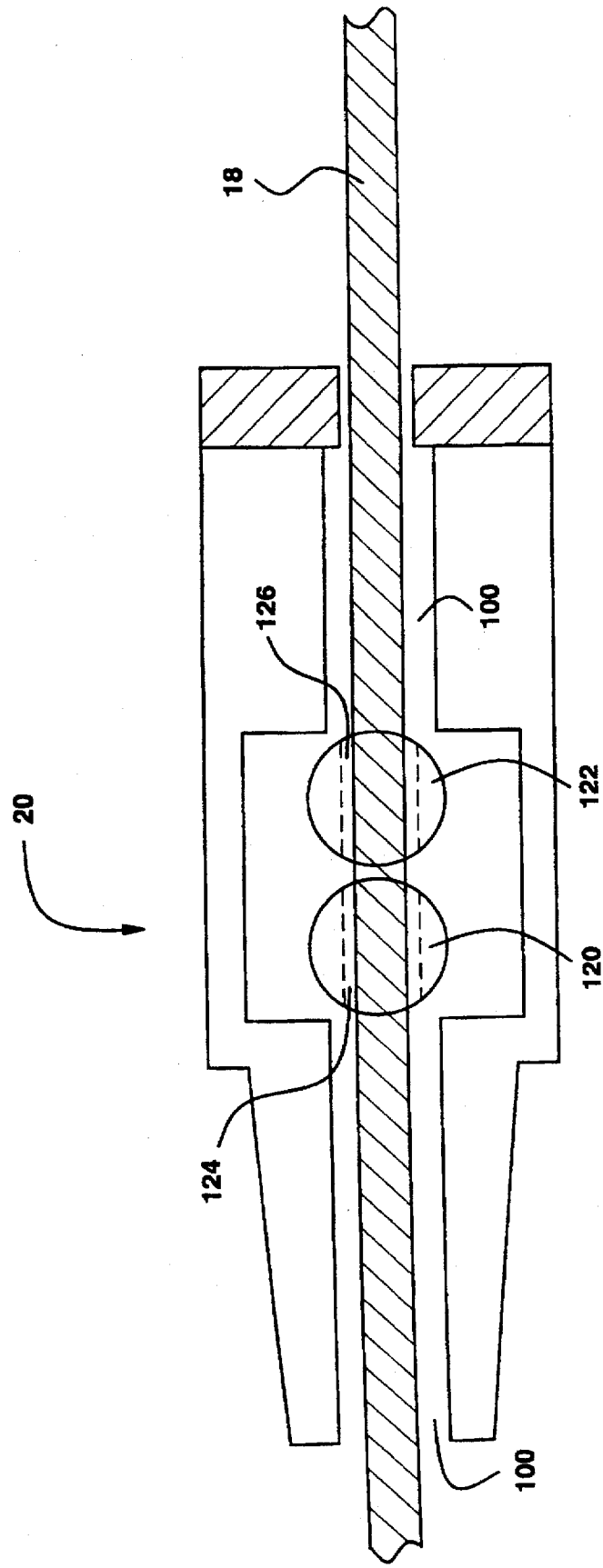
FIG. 4 is a side cross-section view of another aspect of the present invention including a pair of rigid balls with through holes, disposed in the interior chamber, with the cannula in its initial position.
Figure 5:
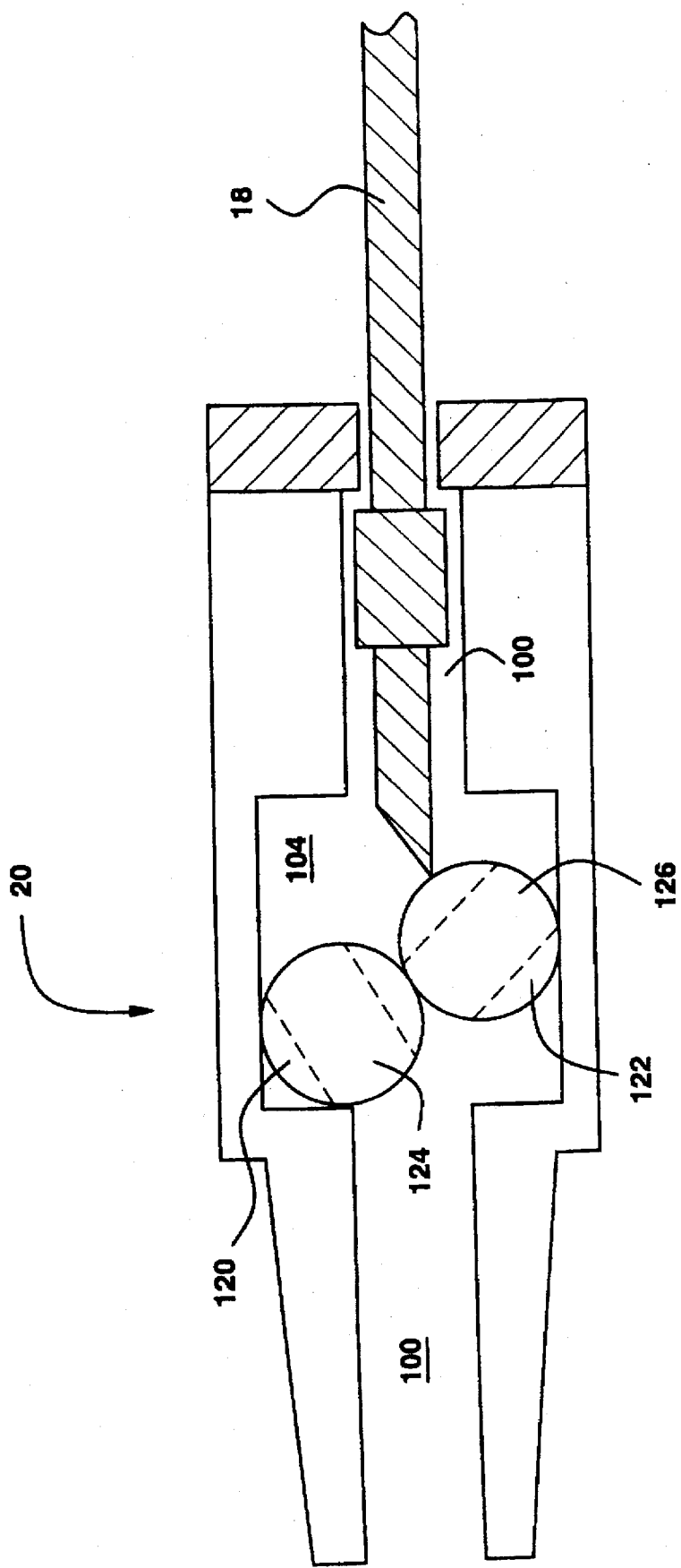
FIG. 5 is a side cross-section view of the aspect of the present invention shown in FIG. 4, wherein the cannula has been retracted and the pair of rigid balls have randomized.

Referring now to FIGS. 4 and 5, a second embodiment of the present invention is provided in cross-section views showing the cannula 18 and the safety cover 20 in the initial and retracted positions, respectively. This embodiment includes a pair of rigid balls 120,122 having through holes 124,126, respectively, in place the rings 108,110 of the first embodiment. More particularly, the safety cover body 20 comprises an axial through hole 100 through which the cannula 18 is disposed in its initial position. In this initial position, each of the spheres 120,122 comprises a through hole 124,126, respectively, which, as shown in FIG. 4, are coaxially aligned with one another having been oriented by the cannula 18. FIG. 5 illustrates the randomized disposition of the spheres 120,122 once the cannula has been removed.

It is understood that the number of rings or spheres utilized is an engineering expedient which does not alter the teachings of the present invention in any way. It is entirely anticipated that one may chose to include a plurality, greater than two, of rings or spheres so that the orientational randomization, and therefore, the prevention of cannula advance, may be more complete.

Figure 6:
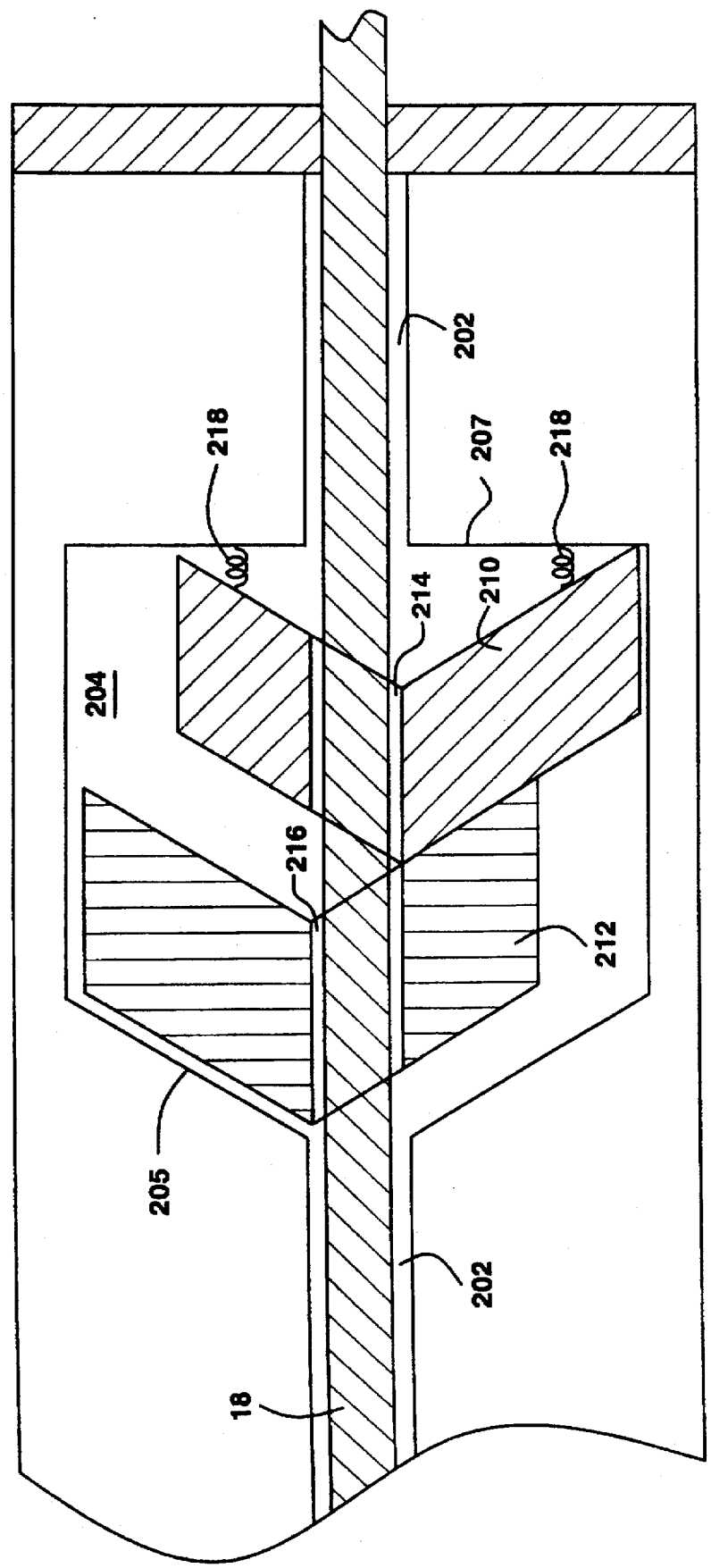
FIG. 6 is a side cross-section view of an aspect of the present invention including a pair of nesting conical elements having offset through holes, disposed in their incomplete nesting position with the cannula in its initial position.
Figure 7:
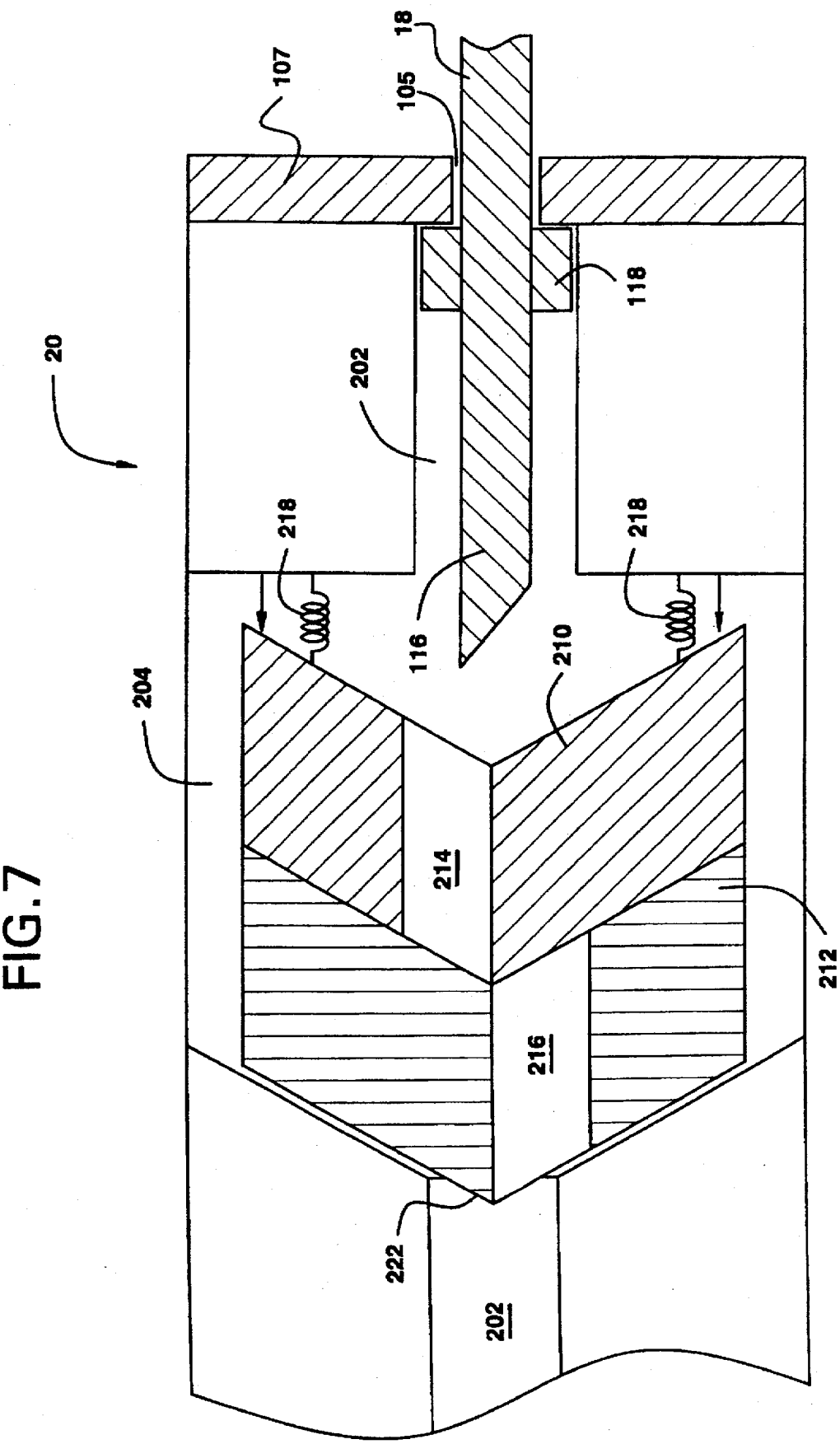
FIG. 7 is a side cross-section view of the aspect of the present invention shown in FIG. 6, wherein the cannula has been retracted and the pair of nesting conical elements have fully nested via spring biasing.

Referring now to FIGS. 6 and 7, a side cross-section view of a third embodiment of the present invention is provided, wherein the safety cover is shown having the cannula in its initial, fully inserted, position and retracted in respective illustrations. With respect to FIG. 6, the safety cover 200 comprises an axial through hole 202, similar to the through hole 100 of the safety cover 20 of the first and second embodiments. In this embodiment, however, the interior chamber 204 has a forward surface 205 which is conical in shape. Within the chamber 204 are a pair of conical elements 210,212. The rear conical section 210 is mounted to the rear surface 207 of the chamber 204 via springs 218 which bias the section 210 forwardly. The forward conical section 212 is positioned so as to receive the rear conical section 210 into a fully nested orientation, and is not otherwise coupled to any fixation means. Each conical element, further, includes a hole 214,216 which is offset from the center line of the, respective, conical element 210,212.

In the initial disposition, with the cannula 18 fully inserted through the safety cover 200 and the holes 214,216 in the conical elements 210,212, the conical elements 210,212 are necessarily displaced relative to their fully nesting position so that the respective holes 214,216 may be axially aligned. As shown in FIG. 6, the forward conical element 212 is displaced upward so that the offset hole 216 therein is aligned with the through hole 202 of the safety cover 200. The rear conical element 210 is correspondingly displaced downward so that its offset hole 214 is also coaxially aligned. In this position, the springs 218, which couple the rear conical element 210 to the rear surface 207 of the chamber 204, are compressed.

Once the cannula 18 is retracted through the holes 214, 216 of the conical element 210,212, as shown in FIG. 7, the biasing springs 218 force the rear conical element 210 forward into its fully nested position with the forward conical element 212. In doing so, the forward conical element 212 is displaced downward, the forwardmost tip 222 thereof entering into the through hole 202, and the rear conical element 210 is translated upward relative to its initial disposition. In this orientation, the offset holes 214,216 of the conical sections 210,212 are no longer aligned relative to one another, nor are they aligned relative to the through hole 202. Further, the cannula 18 may not be advanced forward through the safety cover 200, as the holes through which it had originally translated were misaligned under spring biasing. It is understood that the conical shape of the nesting elements 210,212 prevents the cannula 18 from forcing the elements back into their initial arrangement. It is further understood that the spring biasing provides a force which eliminates any concern that the elements might realign with one another and with the through hole 202, via random motion.

As previously described with respect to the first and second embodiments, it is preferable that the cannula 18 include a thickened portion 118 of the shaft, spaced appropriately from the tip 116 thereof, which is engaged by the narrow diameter of the center hole 105 of the rearwardly disposed annular section 107 so that the thickened portion cannot pass therethrough. As a result, the tip 116 is prevented from fully retracting out of the safety cover 20, but can be retracted far enough that the conical elements may be freed to fully nest.

While there has been described and illustrated specific safety covers for preventing accidental "needle sticks" with contaminated needles, it will be apparent to those skilled in the art that variations and modifications are possible without deviating from the broad spirit and principle of the present invention which shall be limited solely by the scope of the claims appended hereto.

What is claimed is:

1. A safety cover for locking a tip of a cannula therein, comprising:

an elongate body having an interior chamber, said elongate body being slidably mountable on said cannula;

a through hole, extending along the entire axial length of the elongate body, from a forward portion of the body, through said interior chamber and through a rearward portion of said body, said cannula being slidable therethrough; and at least two elements, disposed in said interior chamber, said elements each having a hole for receiving said cannula therethrough, and which displaces upon retraction of the tip of said cannula tip such that subsequent readvancement of said cannula through a forward portion of said safety cover is prevented.

2. The safety cover as set forth in claim 1, wherein said at least one element comprises a plurality of annular rings.

3. The safety cover as set forth in claim 2, wherein said plurality of annular rings comprises a pair.

4. The safety cover as set forth in claim 2, wherein each of said plurality of annular rings has a different outer diameter.

5. The safety cover as set forth in claim 1, wherein said at least one element comprises a plurality of rigid spheres having through holes.

6. The safety cover as set forth in claim 1, wherein said at least one element comprises a pair of rigid spheres.

7. The safety cover as set forth in claim 1, wherein said at least one element comprises a pair of conical elements each having an offset through hole therein.

8. The safety cover as set forth in claim 7, wherein a first one of said pair of conical elements is spring biased within said interior chamber, whereby retraction of said cannula permits said first one of said pair to fully nest within the other of said pair, therein misaligning said offset through holes and preventing subsequent readvancement of said cannula tip through said forward portion of said safety cover.

9. A safety cover for locking a tip of a cannula therein, comprising:

an elongate body having an interior chamber, said elongate body being slidably mountable on said cannula;

a through hole, extending along the entire axial length of the elongate body, from a forward portion of the body, through said interior chamber and through a rearward portion of said body, said cannula being slidable therethrough; and at least two orientationally randomizable elements disposed in said interior chamber, said randomizable elements each having a hole for receiving said cannula therethrough, said elements being orientationally randomized by the retraction of the tip of said cannula so that subsequent readvancement of said cannula tip through said safety cover is prevented.

10. The safety cover as set forth in claim 9, wherein said at least one orientationally randomizable element comprises a plurality of annular rings.

11. The safety cover as set forth in claim 10, wherein said at least one orientationally randomizable element comprises a plurality of rigid spheres having holes therethrough.

12. A safety cover for locking a tip of a cannula therein, comprising:

an elongate body having an interior chamber, said elongate body being slidably mountable on said cannula;

a through hole, extending along the entire axial length of the elongate body, from a forward portion of the body, through said interior chamber and through a rearward portion of said body, said cannula being slidable therethrough; and a pair of displacing elements, disposed in said interior chamber, each of said pair having a hole for receiving said cannula therethrough, wherein at least one of said pair is spring biased such that retraction of the tip of said cannula causes the pair to move relative to one another such that subsequent readvancement of said cannula tip through said safety cover is prevented.

13. A safety cover as set forth in claim 12, wherein said pair of displacing elements comprises a pair of conical elements, each of said conical elements having an offset hole therethrough, and wherein a first of said pair is spring biased relative to the other.

14. A cannula safety assembly, comprising:

an elongate cannula having a tip and a shaft;

an elongate body having an interior cheer, said elongate body being slidably mounted on said shaft of said cannula;

a through hole, extending along the entire axial length of the elongate body, from a forward portion of the body, through said interior chamber and through a rearward portion of said body, said cannula being slidable therethrough; and at least two elements, disposed in said interior chamber, said elements each having a hole for receiving said cannula therethrough, and which displaces upon retraction of the tip of said cannula such that subsequent readvancement of said cannula tip through a forward portion of said safety cover is prevented.

15. The cannula safety assembly as set forth in claim 14, wherein said elongate cannula further comprises a thickened section adjacent to said tip, the through hole extending through said rearward portion having a diameter which is smaller than the diameter of said thickened section of said cannula whereby the tip of the cannula may not be retracted from said elongate body.

* * * * *